US011918722B2

(12) United States Patent
Häcker et al.

(10) Patent No.: US 11,918,722 B2
(45) Date of Patent: Mar. 5, 2024

(54) INSERT PIECE FOR A BLOOD TUBING SET TO PROMOTE MIXING AN INFUSION SOLUTION WITH A FURTHER FLUID

(71) Applicant: Fresenius Medical Care Deutschland GmbH, Bad Homburg (DE)

(72) Inventors: Jürgen Häcker, Neu-Anspach (DE); Jürgen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1027 days.

(21) Appl. No.: 16/335,304

(22) PCT Filed: Sep. 22, 2017

(86) PCT No.: PCT/EP2017/074043
§ 371 (c)(1),
(2) Date: Mar. 21, 2019

(87) PCT Pub. No.: WO2018/055091
PCT Pub. Date: Mar. 29, 2018

(65) Prior Publication Data
US 2020/0016314 A1 Jan. 16, 2020

(30) Foreign Application Priority Data

Sep. 23, 2016 (DE) .......................... 102016117974.4

(51) Int. Cl.
*A61M 1/34* (2006.01)
*A61M 1/36* (2006.01)
*A61M 39/00* (2006.01)

(52) U.S. Cl.
CPC ........ *A61M 1/3465* (2014.02); *A61M 1/3472* (2013.01); *A61M 1/3672* (2013.01);
(Continued)

(58) Field of Classification Search
CPC .............. A61M 1/3465; A61M 1/3472; A61M 1/3672; A61M 2039/0027; A61M 2206/14; A61M 2206/20; A61M 1/342
See application file for complete search history.

(56) References Cited

U.S. PATENT DOCUMENTS

| 3,511,238 A | 5/1970 | Von Wrangell |
| 5,306,265 A | 4/1994 | Ragazzi |

(Continued)

FOREIGN PATENT DOCUMENTS

| CN | 104039375 | 9/2014 |
| DE | 4240681 | 6/1994 |

(Continued)

OTHER PUBLICATIONS

International Search Report and Written Opinion in International Appln. No. PCT/EP2017/074043, dated Dec. 4, 2017, 10 pages (Full English Translation).

(Continued)

*Primary Examiner* — Krishnan S Menon
(74) *Attorney, Agent, or Firm* — Fish & Richardson P.C.

(57) ABSTRACT

The present disclosure relates to an insert piece for a blood tubing set. The insert piece includes at least a first connection site for connecting a first tubing portion of the blood tubing set to the insert piece, and a second connection site for connecting a second tubing portion of the blood tubing set to the insert piece. The insert piece also includes a third connection site for connecting a third tubing portion of the blood tubing set to the insert piece, and a main line for forwarding a first liquid through the insert piece. The main line is in fluid communication with the first connection site and with the second connection site. The insert piece also includes a secondary line for forwarding a second liquid into (Continued)

the main line. The secondary line is in fluid communication with the third connection site.

24 Claims, 8 Drawing Sheets

(52) U.S. Cl.
CPC . *A61M 2039/0027* (2013.01); *A61M 2206/14* (2013.01); *A61M 2206/20* (2013.01)

(56) References Cited

U.S. PATENT DOCUMENTS

| | | | |
|---|---|---|---|
| 9,186,451 B2 | 11/2015 | Beden et al. | |
| 10,315,022 B2* | 6/2019 | Okamoto | A61M 39/045 |
| 2010/0168643 A1 | 7/2010 | Frugier et al. | |
| 2013/0028788 A1 | 1/2013 | Gronau et al. | |
| 2014/0050614 A1 | 2/2014 | Klewinghaus | |
| 2016/0250403 A1 | 9/2016 | Peters | |

FOREIGN PATENT DOCUMENTS

| | | | |
|---|---|---|---|
| DE | 102010047747 | | 4/2012 |
| DE | 102013011010 | | 1/2015 |
| EP | 0165519 | | 12/1985 |
| EP | 1666078 | | 6/2006 |
| EP | 2183004 | | 5/2010 |
| JP | S6337730 U | * | 3/1988 |
| WO | WO 2007/101064 | | 9/2007 |
| WO | WO 2009/030973 | | 3/2009 |
| WO | WO 2014/026771 | | 2/2014 |
| WO | WO 2015/000934 | | 1/2015 |
| WO | WO 2016/206804 | | 12/2016 |

OTHER PUBLICATIONS

International Preliminary Report on Patentability in Application No. PCT/EP2017/074043, dated Mar. 26, 2019, 8 pages (Full English Translation).

International Search Report and Written Opinion in Application No. 23456-0118US1, dated Dec. 4, 2017, 10 pages (Full English Translation).

* cited by examiner

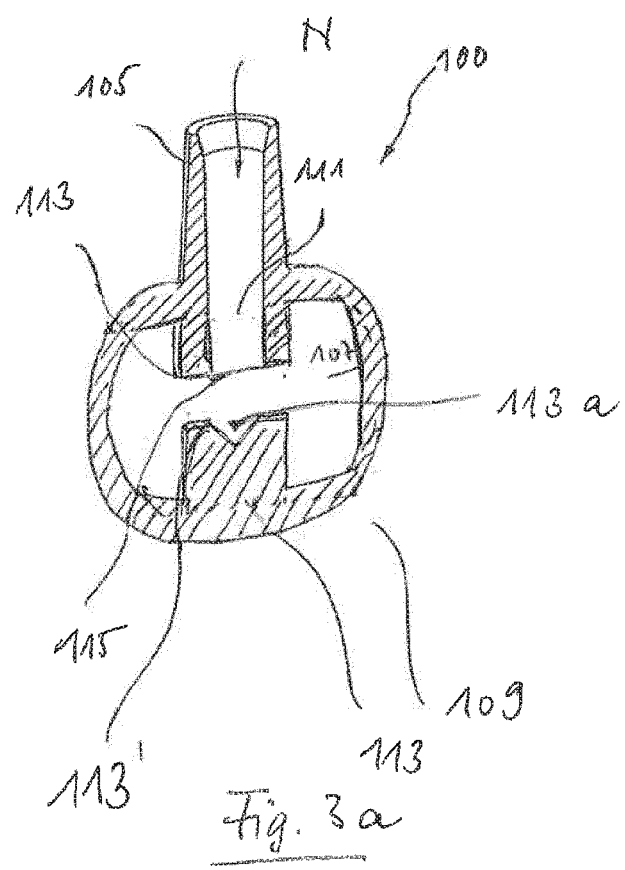

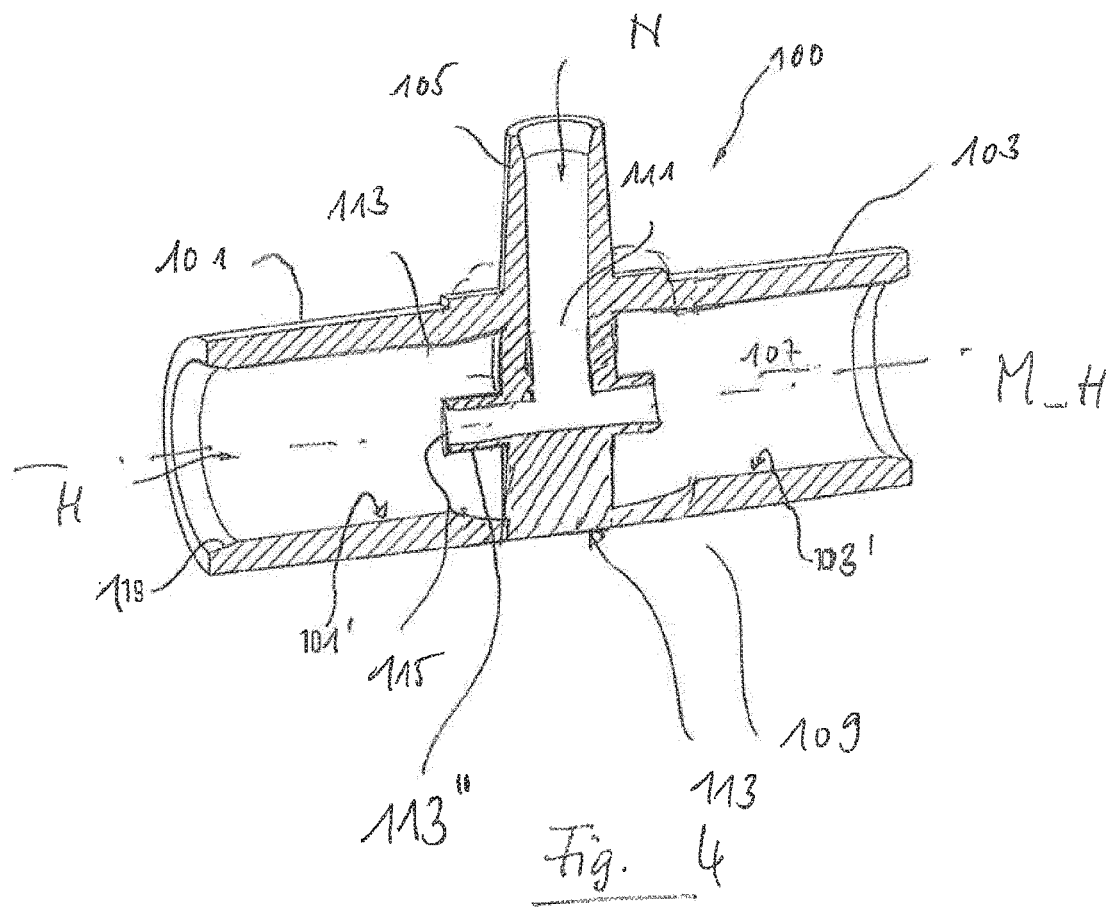

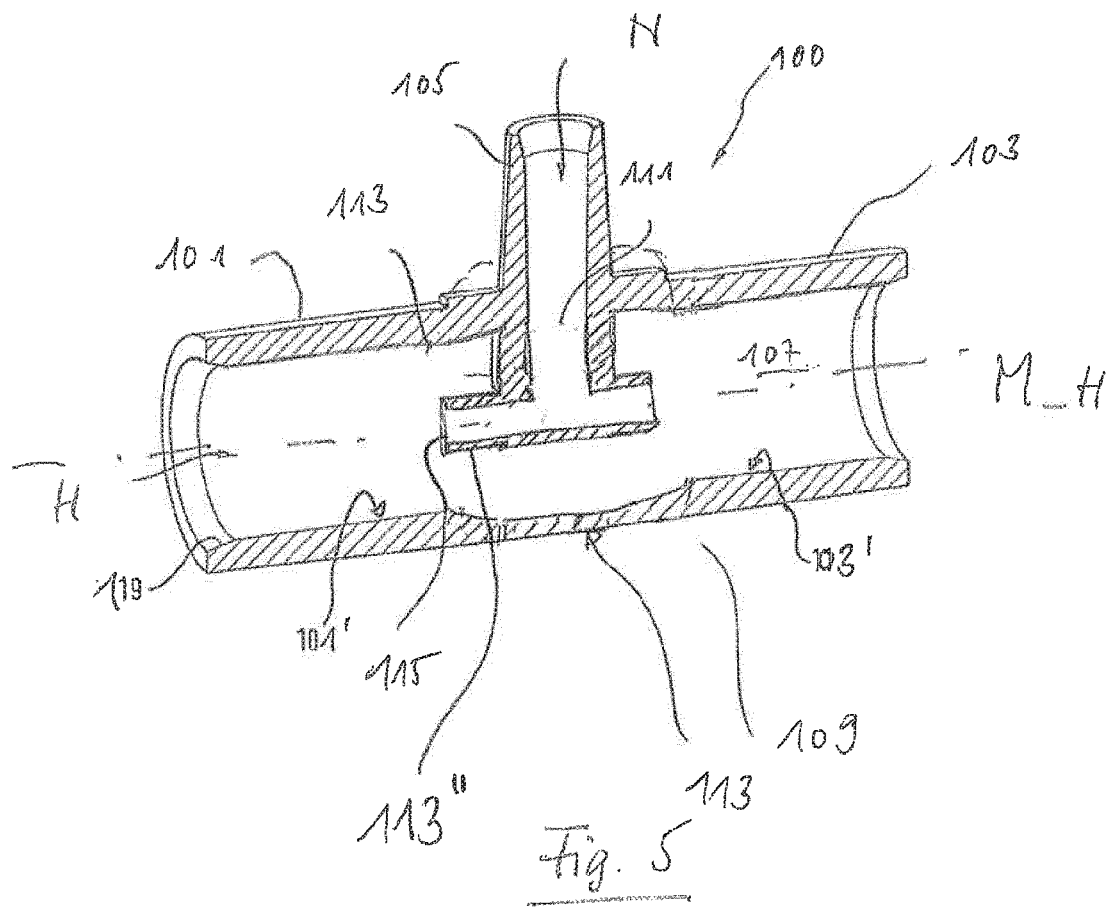

INSERT PIECE FOR A BLOOD TUBING SET TO PROMOTE MIXING AN INFUSION SOLUTION WITH A FURTHER FLUID

CROSS-REFERENCE TO RELATED APPLICATIONS

The present application is the national stage entry of International Patent Application No. PCT/EP2017/074043, filed on Sep. 22, 2017, and claims priority to Application No. DE 10 2016 117 974.4, filed in the Federal Republic of Germany on Sep. 23, 2016, the disclosures of which are expressly incorporated herein in entirety by reference thereto.

TECHNICAL FIELD

The present disclosure relates to an insertion piece, an extracorporeal blood tubing set, and a blood treatment apparatus.

BACKGROUND

During extracorporeal blood treatment, infusion solutions or medicaments are mostly infused through the extracorporeal blood circuit, i.e., the utilized blood tubing system. Depending on the type of the infusion solution, a fast mixing of the infusion solution with the blood may be favorable or desirable.

For example, anticoagulation infusion solutions are regularly infused in an extracorporeal blood treatment to prevent a possible occlusion of the extracorporeal blood circuit.

Two methods are mainly used for this purpose; the system and the regional anticoagulation. A citrate solution, which complexes calcium, and thus suppresses the blood coagulation, is mostly used as an anticoagulant in the regional anticoagulation. Prior to returning blood to the patient, an additional calcium must be substituted, since too-low calcium concentrations influence nerves and muscles, the blood coagulation and functions of lung, heart and kidneys. In the regional anticoagulation, a calcium-containing solution, by which the physiological calcium concentration in the system blood may be maintained, is therefore added to the blood before reinfusing it into the patient.

Infusing infusion solutions or medicaments into the tubing set takes place usually through addition sites with a T-form, the so-called Tees. Laminar flow conditions predominate in these Tees due to the circular cross section and the smooth inner wall at the addition site. In addition, the flow rates of the infused solutions are low in comparison with the blood flow.

The largely laminar flow conditions and the low flow rates of the infusion solutions or medicaments flowing into the blood stream may delay or slow down the mixing of the blood with the added infusion. This slow mixing of both liquids at the addition site is undesired, especially when adding the calcium solution to blood, and may lead to clot problems at the addition site, due to the punctually continued higher calcium concentrations in blood. To prevent that, a fast and homogenous mixing of the added calcium solution with the blood is desirable.

SUMMARY

An insert piece in form of a T-piece having a spiral structure for a blood tubing set is thus described in WO 2014/026771 A1. The spiral structure serves generating turbulences in the area of the infusion site. The turbulences serve or contribute to a better mixing of the fluids, which are brought together.

Furthermore, there are solutions which generate a pulsed infusion flow of the infusion solution into the blood through intermittent operation of an infusion pump. The present disclosure describes further solutions for promoting a mixing of an infusion solution with a further fluid, e.g. blood.

The insert piece according to the present disclosure is intended to be inserted into a blood tubing set (or into a blood tubing system) or to be part thereof, respectively. The insert piece comprises at least a first connection site for connecting a first tubing portion of the blood tubing set to the insert piece. It comprises a second connection site for connecting a second tubing portion of the blood tubing set to the insert piece. It comprises a third connection site for connecting a third tubing portion of the blood tubing set to the insert piece. It comprises a main line for conducting a first liquid, preferably blood, through the insert piece. The main line is in fluid communication with at least the first connection site and with the second connection site or with a lumen surrounded or formed by the first connection site and/or the second connection site.

The insert piece comprises at least one secondary line for conducting, directly or indirectly, a second liquid, preferably an infusion solution, into the main line. The secondary line is in fluid communication with the third connection site or with a lumen surrounded or delimited by it. The secondary line is in fluid communication with the main line in an intermediate portion of the insert piece which intermediate portion being arranged between the first connection site and the second connection site.

The first connection site comprises a perfusable or flow-through lumen having a first cross section area. The second connection site comprises a perfusable or flow-through lumen having a second cross section area. The intermediate portion comprises a perfusable lumen having a third cross section area. The secondary line comprises a lumen portion. The lumen portion comprises at least one opening or outlet opening for the second fluid. The lumen portion protrudes into the interior of the intermediate portion.

The blood tubing set, extracorporeal blood circuit or blood tubing system comprises at least one insert piece.

In some exemplary embodiments, the insert piece is pressed or interposed between tubing portions of the blood tubing set or it is integrally manufactured therewith.

In some exemplary embodiments, the insert piece is firmly connected to the tubing portion of the blood tubing set. In some embodiments, it is releasably connected.

The blood treatment apparatus is connected to at least one blood tubing set.

Embodiments according to the present disclosure may encompass one or several of the aforementioned or following features in any desired combination. Embodiments are moreover subject-matter of the dependent claims.

Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" encompassing "at least one". This understanding is also equally encompassed by the present invention as the interpretation that a numeric word, for example, "one" may alternatively mean "exactly one", wherever this is evidently technically possible for the person skilled in the art. Both are encompassed by the present invention and apply herein to all used numerical words.

Spatial information given herein such as "top," "bottom," etc., refer in case of doubt to the illustrations as seen in the accompanying figures.

In certain exemplary embodiments, the outlet opening opens into (in radial direction) a central area of the perfusable or flow-through lumen or into a central area of the intermediate portion.

In certain exemplary embodiments, the first connection site, the second connection site, and/or the intermediate portion comprise, respectively, a mostly cylindrical inner wall or a section having a cylindrical inner wall.

In certain exemplary embodiments, the insert piece is manufactured integrally with the blood tubing set. All or some of the sections of the insert piece denoted herein as connection sites are in such embodiments passage sections between insert piece and adjacent or continuing tubing portions.

In certain exemplary embodiments, the secondary line is connected in fluid communication with, or comprises, a source for the infusion solution.

In certain exemplary embodiments, the infusion solution is a calcium solution or comprises calcium solution. The present invention is however not limited to using a calcium-containing solution. Other medicament solutions are encompassed by the present invention as well. They include, in particular, citrate solution.

In certain exemplary embodiments, the third cross section area is as big, or substantially as big, as the first cross section area and/or the second cross section area. "Substantially as big" may refer to or take on a value of 80%, 90% or more. All intermediate values and in particular each integer percentage value (81%, 82%, 83%, etc.) are included or contemplated as well.

In certain exemplary embodiments, the lumen portion is embodied such that the second liquid flowing out of the outlet opening is delivered or may be delivered into the main line in, or substantially in, an axial direction of the main line or parallel to a main flow direction of the main line. This design may relate above all to the main flow direction in the intermediate portion. This may be achieved through bending the secondary line in the intermediate portion.

In certain exemplary embodiments, the outlet opening is arranged in order to deliver or bring the second liquid into the main line in an axial direction or in a substantially axial direction of the main line or parallel to a main flow direction of the main line. What is referred to hereby may preferably be the main flow direction in the intermediate portion during use of the insert piece as intended.

In certain exemplary embodiments, a portion of the lumen portion, which neighbors or adjoins the outlet opening for the second liquid, is provided upstream of said outlet opening—with respect to the second liquid when flowing towards the main line. Said portion of the lumen portion is arranged such that its longitudinal direction or its longitudinal axis extends parallel or substantially parallel with the longitudinal axis of the intermediate portion or parallel to a middle line of the main line.

In certain exemplary embodiments, a baffle or deflector element is provided in the area of the intermediate portion and in the interior of the latter. This element is arranged such that a second liquid flowing out of the outlet opening or opening of the secondary line is limited in its radial movement or in its movement in the outlet direction.

In certain exemplary embodiments, the baffle or deflector element is not the inner wall of the main line, for example in the area of the first connection site, of the second connection site or the intermediate portion.

In certain exemplary embodiments, the radial inner end of the baffle or deflector element is disposed further radially to the inside than the inner wall of the main line, for example in the area of the first connection site, the second connection site, or the intermediate portion.

In certain exemplary embodiments, the baffle or deflector element is part of the lumen portion.

In certain exemplary embodiments, the lumen portion extends in one piece or in several pieces through the entire interior of the main line, namely in cross direction or in radial direction.

In certain exemplary embodiments, a protrusion in the area of the intermediate portion extends into the interior of the intermediate portion. The protrusion lies in an extension or in an imaginary continuation of the secondary line in the interior of the intermediate portion.

In certain exemplary embodiments, an addition line is connected in fluid communication to a blood return line and/or to a blood withdrawal line of the blood tubing set via the secondary line of the insert piece.

In certain exemplary embodiments, the blood tubing set is suitable and/or provided for executing a regional anticoagulation.

In certain exemplary embodiments, the blood tubing set is suitable and/or provided for executing a hemodialysis, a hemofiltration or a hemodiafiltration or a plasmapheresis treatment or a whole blood adsorption treatment.

In certain exemplary embodiments, the lumen portion is not a portion which contacts the inner wall of the intermediate portion or which would continue the inner wall. In particular, it is not a portion, which would contact or continue the inner wall without forming thereby a radial step or landing.

In certain exemplary embodiments, the lumen portion protrudes beyond the inner wall and into the interior of the intermediate portion.

In certain exemplary embodiments, the lumen portion—in a cross section of the intermediate portion—has no annular form.

In certain exemplary embodiments, the lumen portion is not a bezel-like or nozzle-like structure.

In certain exemplary embodiments, the lumen portion does not contact—e.g. in a cross section of the intermediate portion—the inner wall of the intermediate portion in a circular form or circularly, i.e. around the whole inner circumference of the intermediate portion.

In certain exemplary embodiments, the lumen portion does not circularly narrow the perfusable or flow-through lumen of the intermediate portion, i.e. around the whole inner circumference of the intermediate portion.

In certain exemplary embodiments, the lumen portion is arranged in the interior of the main line such that liquid flowing through the lumen of the main line may flow, in the area of the lumen portion, in front of the latter (in front of the drawing plane of the accompanying drawing) as well as behind it (i.e. behind the drawing plane of the accompanying drawing).

In certain exemplary embodiments, the lumen portion protrudes in a pen-like or cylinder-like form into the lumen of the main line.

In certain exemplary embodiments, the lumen portion comprises at least a groove, which extends, at least in section or part, in a direction parallel to the main line.

The groove may, for reasons of production, be advantageously exclusively straight. It may have a curved section in longitudinal direction for a better distribution of fluid added through the secondary line.

The groove may have, in a cross section, a curved, triangular, or any other form In certain exemplary embodiments, the insert piece is made of plastic, preferably injection molded.

In certain exemplary embodiments, the insert piece has no three-dimensional spiral structure for generating a turbulence, in particular no recessed section in the inner wall of the intermediate portion.

In certain exemplary embodiments, the lumen portion is not designed as an elevated bulge or bead on the inner wall of the intermediate portion, or is no thickening of the inner wall.

In some exemplary embodiments, the first, the second and/or the third connection site is bonded to a tubing portion, respectively.

In some exemplary embodiments, the blood tubing set comprises a drip chamber, further insert pieces in form of Tees or injection points, etc.

In some exemplary embodiments, the blood tubing set is intended and/or suitable for executing an extracorporeal blood treatment with a regional anticoagulation.

When liquids are mentioned herein, it is not to be understood restrictively. The present invention encompasses or contemplates also bringing together other fluids in a wider sense.

Some or all of the embodiments may include one or several of the aforementioned or following advantages.

One advantage is that no further devices or method steps are required for ensuring a swirling of the infusion solution within the blood due to the injection or introduction of the infusion solution into the blood. Nevertheless, an accelerated and reliable mixing of the infusion solution with the blood may be achieved.

An advantage of using the insert piece according to the present disclosure may further be that the herein described advantages may be achieved without requiring a change in the controlling of the blood treatment apparatus or the pump for the infusion solution. Since the structure of the insert piece effects an advantageous distribution of the second fluid into the first fluid without requiring e.g. a pulsating addition as described in, e.g., DE 10 2013 011 010 A1. The effect may only be achieved by means of the geometry of the insert piece described herein. In particular, no amendments in the controlling of the infusion pump is required. Its conveying characteristic may be maintained.

This advantageously implies that no structural or other type of adjustment of the already delivered blood treatment apparatus, e.g. a software adjustment or modification, is required. The implementation of the present invention may consist of using the insert pieces or blood tubing sets. Switching to such blood tubing sets is also easy to accomplish since they are anyhow single-use articles or disposables.

The effect of the insert piece is independent of parameters of the blood treatment. If for example the conveying rate of the blood pump and the conveying rate of the pump for the infusion solution being in line with the former are changed, then the effect principle or the effect of the insert piece remains unchanged or undisturbed.

Finally, the insert piece convinces or impresses due to its extremely simple and, when desired, even symmetrical design. It can be produced by most simple injection molding tools, which may reduce the total costs of its production significantly. Spiral shapes and contours are dispensable, as are undercuts. Simple, straight walls may prevail at the insert piece.

In some embodiments, the intermediate portion comprises a cross-sectional surface or area that increases, along the intermediate portion, monotonically from one end to the other in one region and decreases monotonically in a second region. Preferably, the cross-sectional surface increases first along the intermediate portion and then decreases again.

In some embodiments, the first and the second region merge into each other directly, so that preferably the cross-sectional surface initially increases along the intermediate portion monotonically and decreases directly thereafter monotonically. In other embodiments, the first region and the second region of the intermediate portion are separated from each other, for example by the secondary line and/or by the baffle or deflector or deflection, preferably exclusively by the secondary line and/or by the baffle or deflector. In this, the cross-sectional surface preferably does not drop or decrease or decline along the intermediate portion below 80%, particularly preferably not below 90%, of the cross-sectional surface of the first and/or second connection site and/or preferably does not rise above 120%, particularly preferably not above 110%, of said cross-sectional surface.

In some embodiments, the cross-section of the first connection site and/or of the second connection site does not decrease in its respective extension or course, in particular not continuously.

In some embodiments, the first connection site and the second connection site are arranged such that they lie on one axis. Preferably, the secondary line is arranged at a right angle to this axis.

In several embodiments, there are no flow obstructions or obstacles inside the insert piece except the secondary line and/or the baffle or the deflector.

Special addition sites, which generate turbulences, are described that advantageously promote mixing of an infusion solution with a further fluid (e.g., blood).

BRIEF DESCRIPTION OF THE FIGURES

The present disclosure is exemplarily explained in the following, regarding the accompanying drawings in which identical reference numerals denote the same or similar elements. The following applies in the partially highly simplified figures:

FIG. 3*a* shows the insert piece of FIG. 3 in a cross section;

FIG. 4 shows a longitudinal cut of an insert piece in a third exemplary embodiment;

FIG. 5 shows a longitudinal cut of an insert piece in a fourth exemplary embodiment.

DETAILED DESCRIPTION OF THE FIGURES

Figure 1:
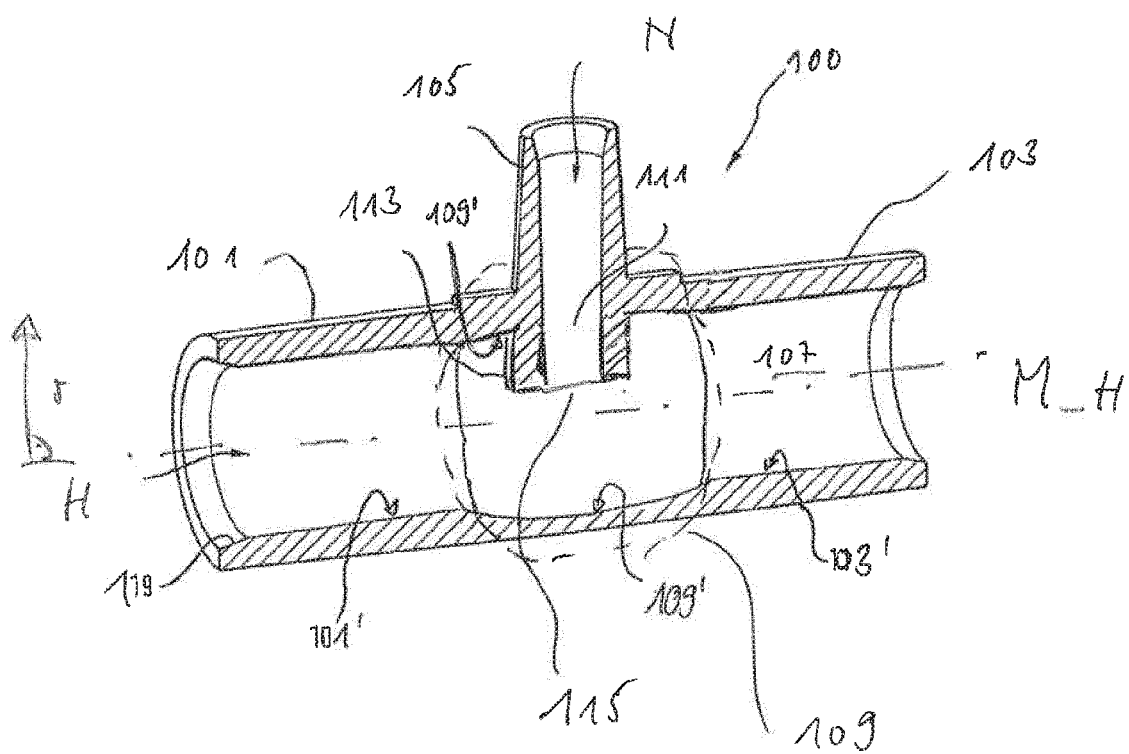
FIG. 1 shows a longitudinal cut of an insert piece for a blood tubing set, not shown in FIG. 1, in a first exemplary embodiment.
Figure 6:
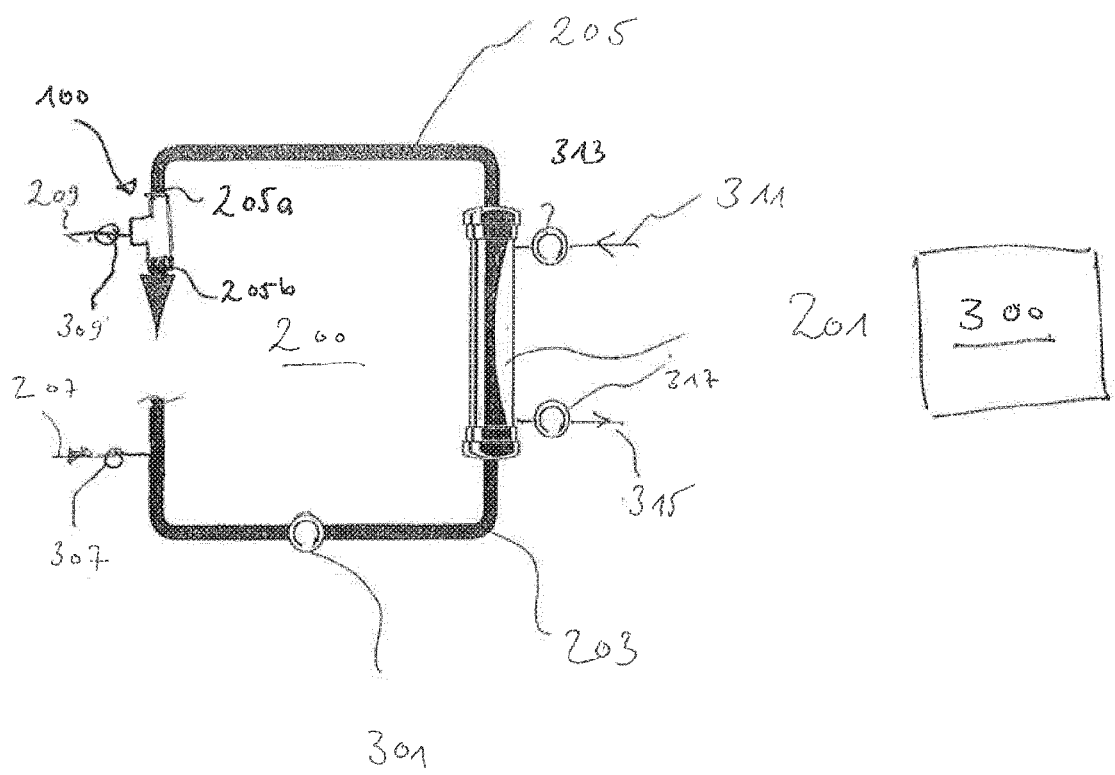
FIG. 6 shows a blood tubing set having an insert piece according to the present disclosure.

FIG. 1 shows a longitudinal cut of the insert piece 100 in a first exemplary embodiment for a blood tubing set 200, not shown in FIG. 1 (see however FIG. 6).

The insert piece 100 comprises a first connection site 101 by means of which a first tubing portion 205*a* (see FIG. 6) of the blood tubing set 200 may be connected to the insert piece 100.

The insert piece 100 comprises a second connection site 103 by means of which a second tubing portion 205b of the blood tubing set 200 may be connected to the insert piece 100.

The insert piece 100 comprises a third connection site 105 by means of which a third tubing portion, here it is a line for calcium solution 209 of the blood tubing set 200, may be connected to the insert piece 100.

The insert piece 100 comprises a main line 107 for conducting a first liquid, preferably blood, through the insert piece 100. The main line 107 is in fluid communication with the first connection site 101 and with the second connection site 103. The first liquid may flow in direction of the arrow H into the main line 107.

The insert piece 100 comprises a longitudinal direction, which extends parallel to the middle line of the main line 107, the latter being denoted with the reference numeral M_H. The insert piece 100 comprises a transverse direction or radial direction, which is denoted with r.

The insert piece 100 comprises an intermediate portion 109, throughout which the main line 107 extends. The intermediate portion 109 is circled with a dashed line in FIG. 1.

The insert piece 100 comprises a secondary line 111. It serves conducting a second liquid, preferably an infusion solution, into the main line 107. The second liquid may flow in direction of the arrow N into the secondary line 111.

The secondary line 111 is in fluid communication with the third connection site 105. It is further in fluid communication with the main line 107 in the intermediate portion 109 of the insert piece 100.

The first connection site 101 comprises a perfusable lumen having a first cross section area and an inner wall 101'. The inner wall 101' encloses an interior of the first connection site 101. The interior in the example of the first connection site 101 is equal to its perfusable lumen.

The second connection site 103 comprises a perfusable lumen having a second cross section area and an inner wall 103'. The inner wall 103' encloses an interior of the second connection site 103. The interior in the example of the second connection site 103 is equal to its perfusable lumen.

The intermediate portion 109 comprises a perfusable lumen having a third cross section area and an inner wall 109'. The inner wall 109' encloses an interior of the intermediate portion 109. The interior in the example of the intermediate portion 109 is not equal to its perfusable lumen. The cross section area of the interior is rather larger than the perfusable cross section area of the lumen by as much as the cross section area of a lumen portion 113, provided the latter extends into the interior. If one imagines that the lumen portion 113 is not shown in FIG. 1, then the interior in FIG. 1 would correspond to the perfusable lumen.

The middle line of the main line 107 (defined e.g. by the middle points of the first and the second cross section areas, see supra) is denoted with M_H. The middle line M_H is equal to the longitudinal axis of the main line 107 and its axial direction.

The secondary line 111 comprises the lumen portion 113 which protrudes into the interior of the intermediate portion 109 and which comprises at least one opening or outlet opening 115. The second liquid may be introduced into the lumen of the main line 107 through the outlet opening 115.

As is seen in FIG. 1, the inner wall 101' encloses or boarders a perfusable lumen or flow-through lumen of the main line 107 in the area of the first connection site 101, while the inner wall 103' encloses a perfusable lumen of the main line 107 in the area of the second connection site 103.

The inner wall 109' encloses a perfusable lumen of the main line 107 in the area of the intermediate portion 109.

As FIG. 1 further shows, the lumen portion 113 protrudes into the interior of the intermediate portion 109. Thereby, the lumen portion 113 is not to be understood as thickening or narrowing of the wall of the insert piece, rather as an opening or break through or continuation of the wall in order to radially place or shift the outlet opening 115 as far as possible into the perfused interior of the main line 107—and thus into the flow of the first liquid through the main line 107.

This may be achieved when, as exemplarily shown in FIG. 1, the diameter of the outlet opening 115 makes up or comprises a major part of the diameter or the cross section area of the lumen portion 113, as this is further explained with reference to FIG. 2.

The first connection site 101, the second connection site 103 and/or the third connection site 105 may optionally comprise, respectively, a chamfer 119 of the inner wall or of the outer wall.

As is seen in FIG. 1, the lumen portion 113 is preferably not a portion which contacts, in a stepless or continuous manner, the inner wall 109' of the intermediate portion 109. While the inner wall 109' limits or borders the interior of the intermediate portion 109, the lumen portion 113 protrudes beyond or above the inner wall 109' into the interior of the intermediate portion 109.

Optionally, the lumen portion 113 is also not a structure being ring-formed in a cross section of the intermediate portion 109.

Optionally, the lumen portion 113 is not a bezel-like or nozzle-like structure which forms an through-opening for the fluid in a cross section of the intermediate portion 109, while it would, at its outer periphery, circularly contact the inner wall 109', i.e. for example contacting the whole inner periphery of the intermediate portion 109.

Optionally, the lumen portion 113 is arranged in the interior of the main line 107 such that the liquid, which perfuses the lumen of the main line 107, may, in the area of the lumen portion 113, flow in front of it (i.e. above the drawing plane) as well as behind it (i.e. behind the drawing plane).

Optionally, the lumen portion 113 protrudes in a pen-like or cylinder-like manner (e.g. with the middle line M_N as a rotation axis) into the interior of the main line 107.

An optional feature of the insert piece 100 is that the perfusable area of the main line 107, in the area of the intermediate portion 109, is not smaller than the perfusable area of the main line in the area of the first connection site 101 and/or in the area of the second connection site 103. Here, several embodiments are contemplated. One option is shown in FIG. 1; the inner wall of the intermediate portion 109 is embodied thinner than the adjacent portions, which leads to enlarging the perfusable lumen by a step-less outer wall. Alternatively or in addition to that, offsetting the wall of the main line 107 in the area of the intermediate portion 109 may be provided such that the inner wall is radially placed to the outside when compared to adjacent areas and such that also the outer wall is radially placed or shifted to the outside when compared to adjacent areas. The latter is not shown in FIG. 1, however, the former is.

Figure 1A:
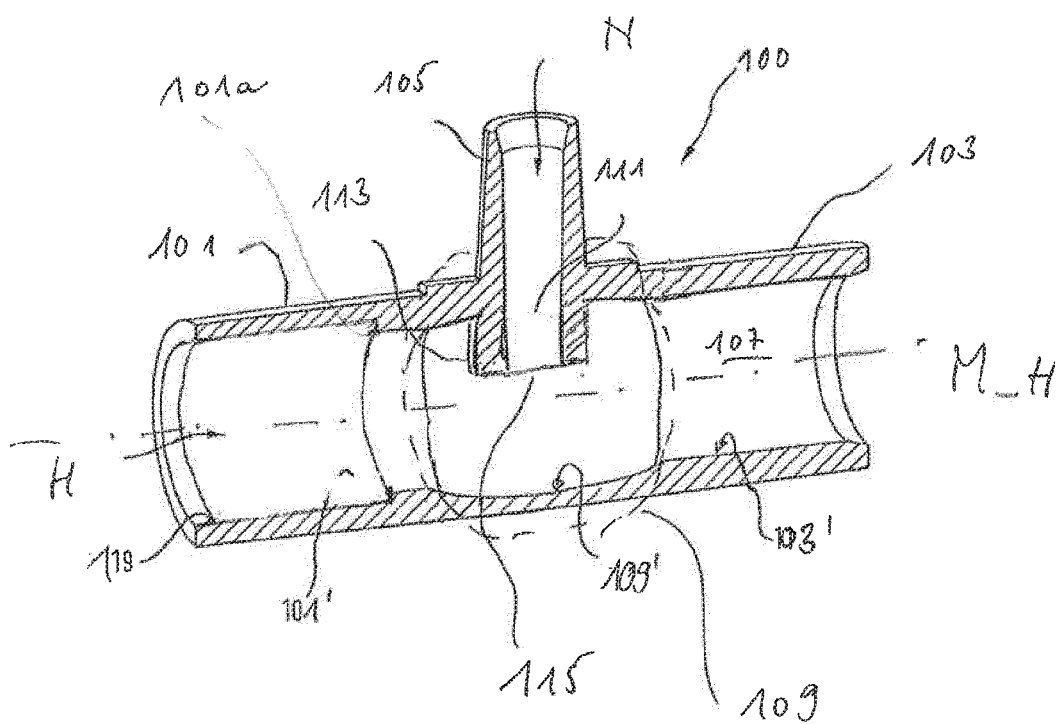
FIG. 1*a* shows the insert piece of FIG. 1 with a slight modification.

FIG. 1*a* shows the insert piece 100 of FIG. 1 with a modification in the left side or arm of the main line 107.

As it is shown with or through the reference numeral 101*a*, the inner wall 101' of the main line 107 comprises a stop, against which a tube (not shown in FIG. 1a), which is inserted into the first connection site 101, may be moved to or pushed to.

The herein exemplarily ring-shaped stop 101a may contact during use the end surface of the likewise ring-shaped tube (not shown). The height of the stop 101a may thereby be advantageously chosen so that the inner wall of the tube step-lessly contacts the inner wall of the section of the inner wall 109' neighboring the stop 101a to the right. In this way, the laminar flow of the fluid in the stagnation area (near the wall) is not undesirably impaired.

In FIG. 1a, such a stop 101a, which may have the form of a step in the inner wall 101', is only shown on the left side of the insert piece 100. Such a stop may however be provided also in the area of the second connection site 103.

Such a stop may further be provided in any other embodiment.

Such a stop may moreover be provided together with a chamfer 119 in any embodiment.

Figure 2:
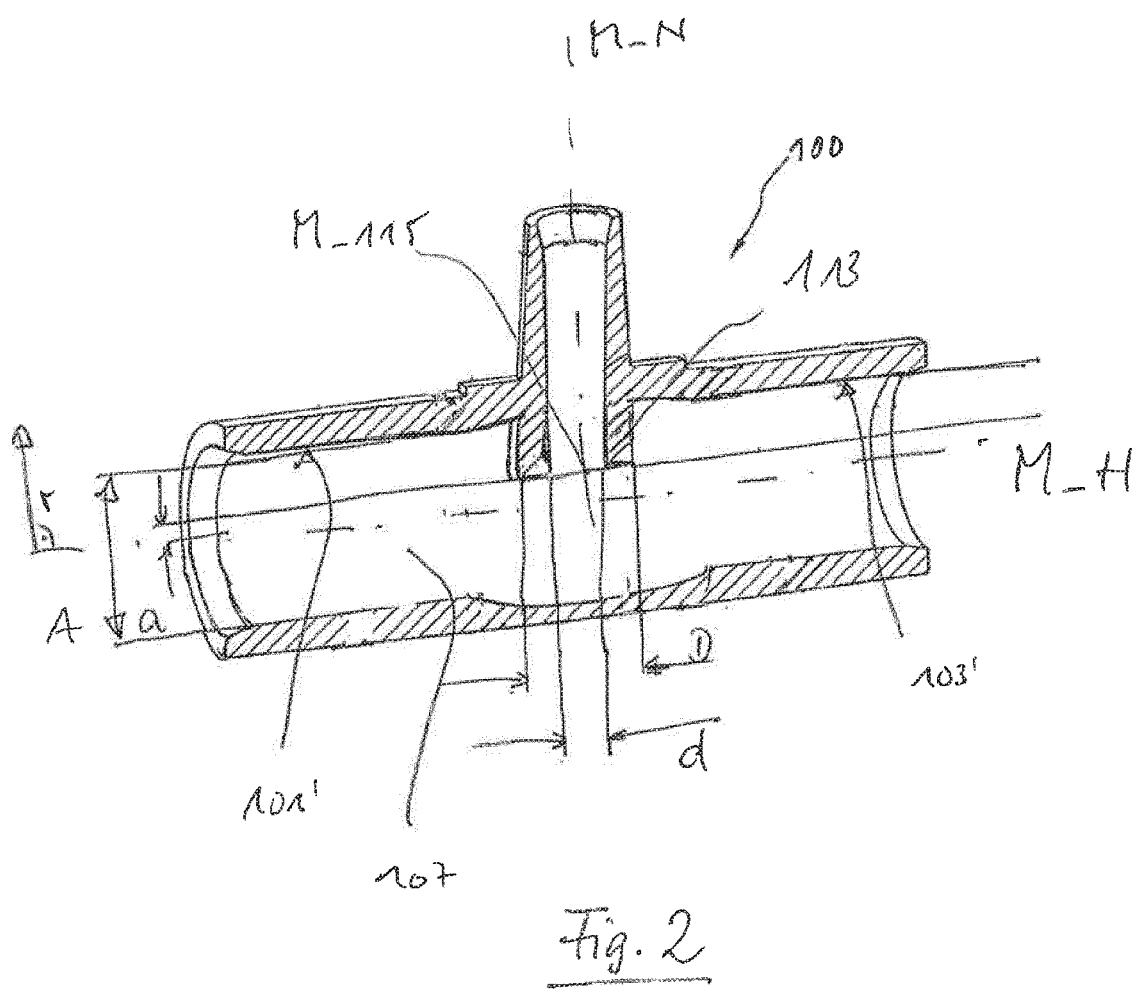
FIG. 2 shows the insert piece of FIG. 1.

FIG. 2 shows the insert piece 100 of FIG. 1. For better clarity, a repeated mentioning of many of the reference numerals already known from FIG. 1 has been omitted.

As is seen, the lumen portion 113 protrudes into the interior of the intermediate portion 109. Thereby, the opening or the outlet opening 115 clearly projects beyond the level of the inner wall 101' or 103' into the interior.

The inner diameter of the main line 107 takes on the value A in the area of the first connection site 101 or in the area of the second connection site 103. The middle point M_115 (or the geometric center) of an opening plane of the outlet opening 115 is disposed apart from the middle line M_H by as much as step a. Thereby, the ratio a/A takes on preferably a maximum of 0.33.

The outer diameter of the secondary line 111 takes on the value D in the area of the outlet opening 115. The inner diameter of the secondary line 111 takes on the value d in the area of the outlet opening 115. Thereby, the ratio d/D is preferably at least 0.125.

Particularly preferred, the ratio a/A has preferably a maximum of 0.17, measured within an area whose points are maximally disposed apart from a middle line M_N of the secondary line 111 by as much as the value 2*d.

The second liquid may be introduced into the lumen of the main line 107 through the outlet opening 115.

Figure 3:
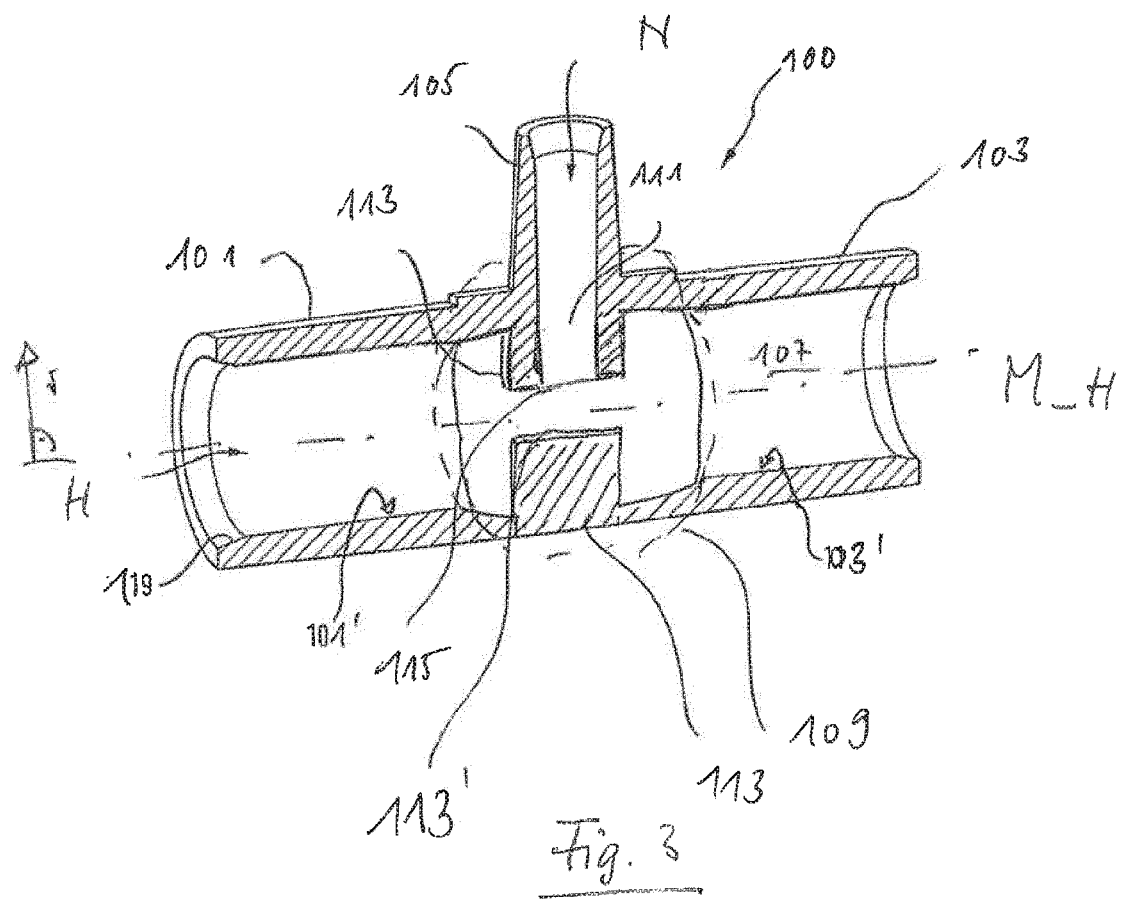
FIG. 3 shows a longitudinal cut of an insert piece in a second exemplary embodiment.

FIG. 3 shows a longitudinal cut of the insert piece 100 for a blood tubing set 200, not shown in FIG. 3, in a second exemplary embodiment.

As is seen in FIG. 3, the lumen portion 113 comprises parts, which reach up or extend to, respectively, both inner wall portions of the main line 107 disposed on opposite sides thereof.

In the example of FIG. 3, a baffle or deflector plate 113' is disposed opposite to the outlet opening 115. The deflector plate 113' is, or may be, part of the lumen portion 113. The deflector plate 113' may serve such that the second liquid when flowing out of the outlet opening 115 is not brought into the radial, outer flow areas (stagnation areas) of the main line 107, rather it flows or enters, closer to the middle line M_H, i.e. in an area with particularly high flow velocity, into the flow of the first liquid.

The embodiment of FIG. 3 represents a more symmetrical embodiment of the insert piece 100 in the area of the intermediate portion 109 than the embodiment of FIG. 1. The embodiment of FIG. 3 may contribute in that the flow through the main line 107 remains untouched as much as possible. In this way the flow profile of the flow through the main line 107 may remain unchanged or undisturbed as much as possible. That way, it is easier to bring the second liquid into the main line 107 in an area having highest flow velocity—with regard to the first liquid of the main line 107—namely into a radially central area of the main line 107.

FIG. 3a shows the insert piece 100 of FIG. 3 in a cross section. The flow through the main line 107 takes place in FIG. 3a mainly into the drawing plane or out of it, i.e. perpendicular to the drawing plane.

The baffle or deflector plate 113', lying opposite to the outlet opening 115, comprises a groove 113a, not seen or recognizable in the view of the FIG. 3. The groove 113a is, or may be, part of the lumen portion 113. It extends preferably in the direction of the flow through the main line 107 and is thus perpendicular to the drawing plane at least in section.

The groove 113a may serve like the deflector plate 113' that the second liquid when flowing out of the outlet opening 115 is not brought until the radial outer flow areas (stagnation areas) of the main line 107. Rather, it flows or enters, closer to the middle line M_H, i.e. in an area with particularly high flow velocity, into the flow of the first liquid and is led into said area, depending on the shape of the groove 113a, along a pre-determined path.

The cross section of the groove 113a may be triangular, as exemplarily shown in FIG. 3a. Other cross section forms are contemplated by the present invention as well.

FIG. 4 shows a longitudinal cut of the insert piece 100 for a blood tubing set 200, not shown in FIG. 4, in a third exemplary embodiment.

As is seen in FIG. 4, the lumen portion 113 further comprises, in addition to the parts known from FIG. 3, a pipe portion 113" arranged in longitudinal direction of the main line 107. The pipe portion 113", may have a round, cross section form. Other arbitrary cross section forms may also be considered and are encompassed by the present invention as well.

In FIG. 4, the longitudinal axis of the pipe portion 113" aligns with the longitudinal direction or, presently, with the middle line M_H of the main line 107. In other embodiments, the longitudinal axis of the pipe portion 113" or its longitudinal direction is parallel to the longitudinal direction or, presently, to the middle line M_H of the main line 107.

Deflecting elements, other than those shown in FIG. 4, for deflecting the liquid flowing out of the secondary line 111 such that it flows out of or exits the outlet opening 115 in or with a, as much as possible, parallel flow direction and flows into the flow of the liquid perfusing the main line 107, are encompassed by the present invention as well.

The deflecting element 113', may advantageously stabilize the flow, depending on the embodiment. It may advantageously contribute to ensuring that the second liquid is indeed brought in or to a middle of the flow profile along or across the cross section or to where the flow velocity within the main line 107 is at least sufficiently high or even at its highest.

The pipe portion 113" may, like the baffle or deflecting plate 113' of FIG. 3, contribute to allowing the outflow of the second liquid out of the outlet opening 115 to take place in an area in which the flow into the main line 107 is not stagnated.

FIG. 5 shows a longitudinal cut of the insert piece 100 for a blood tubing set 200, not shown in FIG. 3, in a fourth exemplary embodiment.

As is seen in FIG. 5, the lumen portion 113 comprises the pipe portion 113" of FIG. 4. Unlike in FIG. 4, the lumen portion 113 does not reach or extend through the entire interior of the intermediate portion 109. The lumen portion 113 reduces therefore the perfusable lumen of the intermediate portion 109 less than in FIG. 4.

The aforementioned figures show embodiments in which the second liquid flows out of the outlet opening 115. The present invention encompasses however also solutions with a plurality of outlet openings 115. Thus, several axially spaced outlet openings may be provided.

FIG. 6 shows an exemplary embodiment of an optional basic arrangement of an insert piece 100 in an extracorporeal blood tubing set 200, the latter being illustrated in a schematically highly simplified manner.

The blood tubing set 200 comprises a hemofilter 201 or is connected thereto. A blood withdrawal line 203 (or arterial line) and a blood return line 205 (or venous line) are connected to the hemofilter 201 or dialyzer or blood filter.

The blood withdrawal line 203 is operatively connected to, or comprises, a blood pump 301.

A further addition line, here a line 207 for citrate solution, opens upstream of the blood pump 301 into the blood withdrawal line 203.

The line 207 is operatively connected to, or comprises, a citrate pump 307.

Downstream of the hemofilter 201, the line 209 for calcium solution opens into the blood return line 205.

The insert piece 100 is operatively connected to a calcium pump 309 or comprises the latter. It is supplied by a source for infusion solution, which is not shown in FIG. 1, herein exemplarily a calcium source. The source may be a bag or a bottle. The infusion solution may optionally be generated on-line; in such case the respective device, in which the infusion solution is generated, is considered as a source.

The operative connection to the calcium pump 309 is to be understood herein as an example. Arranging the insert piece 100 behind another pump than a calcium pump, i.e. for example downstream of a citrate pump like the citrate pump 307 of FIG. 6, is encompassed by the present invention.

The hemofilter 201 is connected to a line 311 for fresh dialysis liquid and to a line 315 for spent dialysate or filtrate. The line 311 is connected to, or comprises, a dialysis liquid pump 313. The line 315 is connected to, or comprises, a filtrate pump 317.

The arrowhead indicates the flow direction when using the blood tubing set 200 as intended.

The blood tubing set 200 shown in FIG. 6 may correspond to a standard extracorporeal blood tubing set and may in particular be suitable for the CVVHD (continuous veno-venous hemodialysis).

The pumps 301, 307, 309, 313, and 317 may be part of a blood treatment apparatus 300, which is only schematically indicated. The same applies for the lines 311 and 315.

LIST OF REFERENCE NUMERALS

100 insert piece
101 first connection site
101' inner wall
103 second connection site
103' inner wall
105 third connection site
107 main line
109 intermediate portion
109' inner wall
111 secondary line
113 lumen portion
113' baffle or deflector plate
113" pipe portion
113a groove
115 outlet opening or outlet
119 chamfer
200 blood tubing set, blood tubing system
201 hemofilter or blood filter or dialyzer
203 blood withdrawal line
205 blood return line
205a first tubing portion
205b second tubing portion
207 line for citrate solution
209 line for calcium solution; addition line; third tubing portion
300 blood treatment apparatus
301 blood pump
307 citrate pump
309 calcium pump
311 line for fresh dialysis liquid
313 pump for fresh dialysis liquid
315 line for spent dialysate, or filtrate
317 pump for spent dialysate, or filtrate
A value
a step
D outer diameter of the secondary line
d inner diameter of the secondary line
H inflow direction of the first fluid into the main line
N inflow direction of the second fluid into the secondary line
M_H middle line of the main line
M_N middle line of the secondary line
M_115 middle point of an opening plane of the outlet opening
r radial direction or extension of the main line

The invention claimed is:

1. An insert piece for a blood tubing set, the insert piece comprising:
a first connection site for connecting a first tubing portion of the blood tubing set to the insert piece;
a second connection site for connecting a second tubing portion of the blood tubing set to the insert piece;
a third connection site for connecting a third tubing portion of the blood tubing set to the insert piece;
a main conduit for conducting a first fluid through the insert piece, wherein the main conduit extends between the first connection site and the second connection site; and
a secondary conduit for conducting a second fluid into the main conduit, wherein the secondary conduit extends between the third connection site and the main conduit and is arranged between the first connection site and the second connection site,
wherein the first connection site comprises a perfusable lumen having a first cross section area, wherein the second connection site comprises a perfusable lumen having a second cross section area, wherein the main conduit comprises a perfusable lumen having a third cross section area,
wherein the secondary conduit extends into the perfusable lumen of the main conduit without crossing a center line of the main conduit and comprises an outlet for the second fluid,
wherein the secondary conduit is the only flow obstruction in the main conduit, and
wherein the first connection site, the second connection site, the third connection site, the secondary conduit, and the main conduit are each portions of a single unitarily constructed part.

2. The insert piece according to claim 1, further comprising an infusion fluid source and wherein the secondary conduit is connected in fluid communication with, or is a part of, the infusion fluid source.

3. The insert piece according to claim 1, wherein the third cross section area is substantially equal to the first cross section area and the second cross section area.

4. The insert piece according to claim 1, wherein the third cross section area is substantially equal to the first cross section area or the second cross section area.

5. The insert piece according to claim 1, wherein the secondary conduit is configured to deliver the second fluid into the main conduit in an axial direction.

6. The insert piece of claim 1, wherein the secondary conduit is configured to deliver the second fluid into the main conduit parallel to a main flow direction of the main conduit.

7. The insert piece according to claim 1, wherein the outlet is arranged to pass the second fluid into the main conduit in an axial direction of the main conduit or parallel to a main flow direction of the main conduit.

8. The insert piece according to claim 1, wherein a portion of the secondary conduit is arranged such that a longitudinal direction of the portion of the secondary conduit extends parallel to a longitudinal axis of the main conduit, wherein the portion of the secondary conduit is adjacent the outlet and is upstream of the outlet relative to a flow direction.

9. The insert piece according to claim 1, wherein a deflector element is arranged in the perfusable lumen of the main conduit such that the second fluid flowing out of the outlet of the secondary conduit has limited radial movement.

10. The insert piece according to claim 1, wherein a lumen portion of the secondary conduit extends through the main conduit.

11. The insert piece according to claim 1, further comprising at least one groove, which extends in a direction parallel to the main conduit.

12. The insert piece according to claim 1, wherein a protrusion extends into the perfusable lumen of the main conduit, the protrusion being disposed in an extension of the secondary conduit.

13. A blood tubing set or an extracorporeal blood circuit comprising:
at least one insert piece comprising:
a first connection site for connecting a first tubing portion of the blood tubing set or the extracorporeal blood circuit to the insert piece;
a second connection site for connecting a second tubing portion of the blood tubing set to the insert piece;
a third connection site for connecting a third tubing portion of the blood tubing set to the insert piece;
a main conduit for conducting a first fluid through the insert piece, wherein the main conduit extends between the first connection site and the second connection site; and
a secondary conduit for conducting a second fluid into the main conduit, wherein the secondary conduit extends between the third connection site and the main conduit and is arranged between the first connection site and the second connection site,
wherein the first connection site comprises a perfusable lumen having a first cross section area, wherein the second connection site comprises a perfusable lumen having a second cross section area, wherein the main conduit comprises a perfusable lumen having a third cross section area,
wherein the secondary conduit extends into the perfusable lumen of the main conduit without crossing a center line of the main conduit and which comprises at least an outlet for the second fluid,
wherein the secondary conduit is the only flow obstruction in the main conduit, and
wherein the first connection site, the second connection site, the third connection site, the secondary conduit, and the main conduit are each portions of a single unitarily constructed part.

14. The blood tubing set according to claim 13, wherein the insert piece is connected in fluid communication with an addition line and with a first tubing portion and with a second tubing portion.

15. The blood tubing set according to claim 13, wherein the insert piece is connected in fluid communication with an addition line and with a blood withdrawal line or with a blood return line.

16. The blood tubing set according to claim 13, wherein the first connection site and the second connection site are connected to blood-conducting lines of the blood tubing set, and wherein the third connection site is connected to a line for an electrolyte solution.

17. A blood treatment apparatus, connected to at least a blood tubing set comprising:
an insert piece comprising:
a first connection site for connecting a first tubing portion of the blood tubing set to the insert piece;
a second connection site for connecting a second tubing portion of the blood tubing set to the insert piece;
a third connection site for connecting a third tubing portion of the blood tubing set to the insert piece;
a main conduit for conducting a first fluid through the insert piece, wherein the main conduit extends between the first connection site and the second connection site; and
a secondary conduit for conducting a second fluid into the main conduit, wherein the secondary conduit extends between the third connection site and the main conduit and is arranged between the first connection site and the second connection site,
wherein the first connection site comprises a perfusable lumen having a first cross section area, wherein the second connection site comprises a perfusable lumen having a second cross section area, wherein the main conduit comprises a perfusable lumen having a third cross section area,
wherein the secondary conduit extends into the perfusable lumen of the main conduit without crossing a center line of the main conduit and comprises at least one an outlet for the second fluid,
wherein the secondary conduit is the only flow obstruction in the main conduit, and
wherein the first connection site, the second connection site, the third connection site, the secondary conduit, and the main conduit are each portions of a single unitarily constructed part.

18. The insert piece according to claim 1, wherein:
the outlet of the secondary conduit is spaced apart from the center line of the main conduit by a first distance (a);
an inner diameter of the main conduit corresponds to a second distance (A); and
a ratio of the first distance to the second distance (a/A) is less than 0.33.

19. The insert piece according to claim 18, wherein the ratio of the first distance to the second distance (a/A) is less than 0.17.

20. The insert piece according to claim 1, wherein:
the secondary conduit defines an inner diameter (d) proximate the outlet and an outer diameter (D) proximate the outlet; and
a ratio of the inner diameter to the outer diameter (d/D) is greater than or equal to 0.125.

21. The blood tubing set according to claim 13, wherein the third cross section area is substantially equal to the first cross section area and the second cross section area.

22. The blood tubing set according to claim 13, wherein the third cross section area is substantially equal to the first cross section area or the second cross section area.

23. The blood treatment apparatus according to claim 17, wherein the third cross section area is substantially equal to the first cross section area and the second cross section area.

24. The blood treatment apparatus according to claim 17, wherein the third cross section area is substantially equal to the first cross section area or the second cross section area.

* * * * *